United States Patent [19]

Ando et al.

[11] 4,411,815

[45] Oct. 25, 1983

[54] PROCESS FOR PREPARING ODORLESS ALKYL ETHER SULFATE CONCENTRATES

[75] Inventors: Hideo Ando, Tokyo; Akira Hayashi, Yachiyo; Kyozo Kitano, Narashino, all of Japan

[73] Assignee: Lion Corporation, Tokyo, Japan

[21] Appl. No.: 276,734

[22] Filed: Jun. 24, 1981

[30] Foreign Application Priority Data

Jul. 4, 1980 [JP]  Japan .................................. 55-90730

[51] Int. Cl.³ .............................................. B01F 17/02
[52] U.S. Cl. .................................. 252/353; 252/355; 252/DIG. 1
[58] Field of Search ................. 252/353, DIG. 1, 550, 252/555, 355, 8.55 D; 260/458 R

[56] References Cited

U.S. PATENT DOCUMENTS

| | | | |
|---|---|---|---|
| 3,391,750 | 7/1968 | Ziha et al. | 252/353 |
| 3,893,940 | 7/1975 | Ohogoshi et al. | 252/353 |
| 4,217,296 | 8/1980 | Berkowitz | 252/353 |
| 4,293,428 | 10/1981 | Gale et al. | 252/353 |
| 4,310,471 | 1/1982 | Oswald et al. | 252/353 |

*Primary Examiner*—Josephine Barr
*Attorney, Agent, or Firm*—Flynn, Thiel, Boutell & Tanis

[57] ABSTRACT

An odorless polyoxyethylene alkyl ether sulfate concentrate having a concentration of about 85 wt. % or more can be obtained by treating a polyoxyethylene alkyl ether sulfate aqueous solution having a concentration of about 60–80 wt. % under reduced pressure and at a temperature of 50°–130° C.

8 Claims, No Drawings

PROCESS FOR PREPARING ODORLESS ALKYL ETHER SULFATE CONCENTRATES

BACKGROUND OF THE INVENTION

The present invention relates to a process for preparing a deodorized alkyl ether sulfate aqueous concentrate which comprises treating a high-concentration alkyl ether sulfate aqueous solution under reduced pressure to thereby achieve its deodorization and concentration simultaneously.

As a means for obtaining a high concentration alkyl ether sulfate aqueous solution there is known for instance a process which comprises concentration a low concentrated alkyl ether sulfate aqueous solution by means of a rotary thin film type evaporator as disclosed in Japanese Published Examined Patent Application No. 29304/1978, and a process for obtaining a high concentration alkyl ether sulfate aqueous solution by mixing an excess of alkali-containing alky ether sulfate with a non-neutralizer as disclosed in Japanese Published Unexamined Patent Application No. 64564/1980.

Alkyl ether sulfate contains odorous components such as alcohol, which is itself odorous, cyclic ether which is by-produced in a small quantity during the sulfation reaction and the like. U.S. Pat. No. 3,893,940 discloses a process for removing unreacted oils from the sulfonates or sulfates of olefins having 12 to 22 carbon atoms, paraffins having 12 to 22 carbon atoms and aliphatic monohydric alcohols having 8 to 22 carbon atoms, adding polyhydric alcohol, alcohol ethoxylate or the like to the starting material and treating the resulting mixture at reduced pressure. The concentration of the starting sulfate or sulfonate in this instance, however, is not high, such as 27% or so.

As a matter of course, it is true in the case of an alkyl ether sulfate aqueous solution that the more concentrated the solution the more profitable it is from the viewpoint of far wider application, transportation or storage. However, it is noted in the preparation of alkyl ether sulfate that with the increase of its concentration, the quantities of hydrolysis product of alkyl ether sulfate, cyclic ether and the like also increase. And, in the case of an alkyl ether sulfate aqueous solution, its viscosity also increases rapidly with the increase of its concentration. Due to this, it has been considered difficult to remove said odorous components efficiently under high concentration conditions, and thus the means for deodorization has not been pursued up to now as the subject of investigation.

SUMMARY OF THE INVENTION

An alkyl ether sulfate aqueous solution (or paste-like mixture) is so highly viscous that it almost gels when its concentration is in excess of 40 wt.% and thus loses its fluidity. When the concentration further increases and exceeds a level of 50 wt.%, said solution again displays fluidity, though highly viscous, and displays its minimum viscosity value in the vicinity of about 70 wt.%. Thereafter, the viscosity of the solution begins to increase again. The inventors have achieved the present invention by treating a high concentration alkyl ether sulfate thermally under reduced pressure on the assumption that the so-called reversed micelle is formed in the region where the solution displays fluidity at said high concentration, said reversed micelle being comprised of a continuous phase consisting of alkyl ether sulfate and a dispersion phase consisting of water, and further on the basis of a judgment that odorous components dissolve in the continuous phase and so the vapor pressure therein is comparatively high in the case of this reversed micelle.

In other words, the present invention has succeeded in providing a process for preparing an alkyl ether sulfate aqueous concentrate comprising treating an about 60–80 wt.% aqueous solution of alkyl ether sulfate under reduced pressure at a temperature of 50°–130° C., said alkyl ether sulfate having the general formula $RO(CH_2CH_2O)_nSO_3M$, wherein R represents an alkyl group having 8–18 carbon atoms, n represents an average addition molar number such as about 2–10, and M represents a cation producing a water soluble salt. The high concentration alkyl ether sulfate aqueous solution is subjected directly to deodorizing treatment and simultaneously the concentration of the alkyl ether sulfate aqueous solution is further increased.

DETAILED DESCRIPTION OF THE INVENTION

The alkyl ether sulfate to be treated by the present invention is represented by the aforesaid general formula $RO(CH_2CH_2O)_nSO_3M$, and is normally defined to be the sodium, potassium, magnesium or mono-, di- or triethanol amine salt of a mixture of polyoxyethylene alkyl ether sulfates, the carbon number of the alkyl group and the average mole number of added ethylene oxide thereof being different from each other, typically one to be used as a surface active agent.

The alkyl ether sulfate to be treated according to the present invention preferably has a concentration of about 60–80 wt.%. If the concentration is in the vicinity of 60% or less the viscosity is so high that the deodorizing efficiency is deteriorated, while if the concentration is about 80% or more the viscosity increases during the deodorizing operation thereby to hamper the achievement of sufficient deodorizing effects. One reason for defining this upper limit of the concentration is that it is difficult to obtain an alkyl ether sulfate aqueous solution having a high concentration of 80% or more by ordinary means. This alkyl ether sulfate aqueous solution having a concentration of about 60–80 wt.% can be prepared by the method, as disclosed for instance in Japanese Published Unexamined Patent Application No. 64564/1980, of mixing an excess of alkali-containing polyoxyethylene alkyl ether sulfate with a non-neutralized polyoxyethylene alkyl ether sulfate at a temperature of 30°–60° C. in the presence or absence of a small quantity of citric acid or citrate. However, it is to be noted that the alkyl ether sulfate aqueous solution suitably treated according to the present invention should not be limited only to that prepared by the above-mentioned method. In other words, every alkyl ether sulfate aqueous solution having a concentration of about 60–80 wt.% prepared according to any conventional method in this art can be treated by the process of the present invention.

The deodorizing treatment according to the present invention is carried out under reduced pressure at a temperature of 50°–130° C., preferably 70°–120° C. When the temperature is 50° C. or less, the viscosity is too high to achieve a deodorizing effect, while when the temperature is 130° C. or more, undesirable hydrolysis and coloration of alkyl ether sulfate take place to thereby deteriorate its quality, and simultaneously the odor is rather increased. And, the processing pressure should be in the range of 50–400 mmHg, preferably 200 mmHg or less. In view of the fact that a limitation is put on the deodorizing temperature, the lower the pressure is, the better the results achieved. However, if the temperature is too low, the vapor pressure is also lower. Therefore, it may be said that the actual lower limit of the processing pressure is about 50 mmHg.

It is preferable that the deodorizing operation should be carried out in a short time. Even when the deodorizing operation is conducted at a temperature of 130° C. or less, a prolonged deodorizing time entails a danger of causing hydrolysis and coloration of the alkyl ether sulfate, whereby further foul odor is emitted. Although various kinds of apparatuses are employable for this treating purpose, generally speaking, a thin film type evaporator seems to be suitable for the purpose of treating a relatively highly viscous substance, for instance, such as the object being treated by the present invention.

In the case of the present invention, water also evaporates simultaneously with the deodorizing operation, and thus the alkyl ether sulfate aqueous solution is further concentrated. Despite this, the deodorizing efficiency remains unchanged because the viscosity increases slowly. The alkyl ether sulfate aqueous solution may be concentrated to an extent of at least 5 wt.% or more, although the concentration degree is variable depending on the hours required for treating operation. Accordingly, the present invention can achieve extremely superior results because the present process can readily produce concentrates of little odor concentrated to about 80 wt.% as well as up to about 90 wt.%, as compared with the neutralization method by which it was difficult to obtain a concentration of about 80 wt.% even through a series of contrivances devoted to improvement of viscosity, removal of neutralization heat, prevention of hydrolysis, prevention of coloration and so forth.

DESCRIPTION OF THE PREFERRED EMBODIMENTS

Example

Synthesis of alkyl ether sulfate

By adding ethylene oxide to a synthetic alcohol having 12–13 carbon atoms and 80% straight chain rate there was obtained alcohol ethoxylate having an average ethylene oxide addition number of 5. This alcohol ethoxylate was sulfated with 1.1 moles of sulfur trioxide diluted with inert gas by means of a thin film type sulfation device. Subsequently, this sulfated alcohol ethoxylate was neutralized at a temperature of 30°–50° C. with sodium hydroxide solutions having different concentrations, thereby obtaining sodium alkyl ether sulfate aqueous solutions having concentrations corresponding to different alkali concentrations. By repeating the same procedure there were obtained alkyl ether sulfate aqueous solutions being different respectively in respect of the number of carbon atoms of each alkyl group or the average ethylene oxide addition mol-number or the alkali used.

The thus obtained alkyl ether sulfate aqueous solutions were found to have properties as shown in Table 1.

TABLE 1

| Kind of alkyl ether sulfate | A | B | C | D | E | F*3 | G | H | I | J |
|---|---|---|---|---|---|---|---|---|---|---|
| Number of carbons of alkyl group | 9–11 | 12–13 | 12–13 | 12–13 | 12–13 | 12–13 | 12–13 | 12–13 | 12–13 | 14–15 |
| Average addition of ethylene oxide | 8 | 8 | 3 | 3 | 3 | 5 | 5 | 5 | 5 | 5 |
| Counter ion | Na | Na | K | TEA*4 | Na | Na | Na | Na | Mg | Na |
| Concentration of alkyl ether sulfate aqueous solution (wt. %) | 70 | 63 | 63 | 65 | 25 | 50 | 75 | 85 | 75 | 77 |
| Color tone*1 | 15 | 19 | 17 | 17 | 17 | — | 17 | 23 | 18 | 20 |
| Viscosity (50° C., poise) | 150 | 150 | 150 | 70 | 1 | — | 170 | 300 | 200 | 200 |
| Odor*2 | x | x | x | x | x | — | x | xx | x | x |

(Note)
*1 Absorbancy was measured on a 10 wt. % alkyl ether sulfate aqueous solution and expressed in terms of -logT × 10³.
*2 Organoleptic valuation
o: Nearly odorless
x: Strong foul odor
xx: Very strong foul odor
*3 It gelled and could not be neutralized.
*4 TEA represents triethanolamine salt.

Deodorizing treatment

The alkyl ether sulfate aqueous solutions shown in Table 1 were supplied at a feed rate of 40 Kg/hr to a thin film type evaporator having an evaporation area of 0.1 m² and concentrated for deodorizing purposes. The treating conditions at that time and properties of the resulting products are as shown in Table 2.

TABLE 2

| | Run No. | | | | | | | | | | |
|---|---|---|---|---|---|---|---|---|---|---|---|
| | 1 | 2 | 3*2 | 4 | 5 | 6 | 7*3 | 8 | 9 | 10 | 11 |
| Kind of alkyl ether sulfate | A | A | A | B | C | D | E | G | H | I | J |
| Treating temperature (°C.) | 30 | 120 | 150 | 100 | 100 | 100 | 100 | 100 | 100 | 100 | 120 |
| Treating pressure (mmHg) | 70 | 150 | 200 | 50 | 70 | 50 | 100 | 100 | 100 | 50 | 70 |
| Concentration of product (wt. %) | 79 | 88 | 90 | 85 | 85 | 86 | — | 90 | 95 | 93 | 96 |
| Color tone*1 | 15 | 15 | 21 | 19 | 18 | 18 | — | 17 | 24 | 18 | 22 |
| Viscosity (70°C., poise) | 200 | 7 | 4 | 250 | 230 | 130 | — | 3 | 5 | 5 | 10 |
| Odor*1 | x | o | x | o | o | o | — | o | x | o | o |
| Collective valuation | x | o | x | o | o | o | x | o | x | o | o |

(Note)
*1 Both color tone and odor were valued according to the same procedure as employed in the preceding synthesis example.
*2 The treating temperature was so high that a part (about 3%) of the alkyl ether sulfate decomposed.
*3 It bubbled so violently during treatment that deodorizing concentration treatment could not be effected.

It is evident from the results shown in Table 1 and Table 2 that by heat treatment of the alkyl ether sulfate aqueous solution having a concentration of 63-77 wt.% under 50-150 mmHg pressure, said aqueous solution is deodorized as well as concentrated to 85-96 wt.% (see Run Nos. 2, 4-6, 8, 10 and 11). By contrast, when the alkyl ether sulfate aqueous solution undergoing heat treatment under reduced pressure has a low concentration (Run No. 7) it bubbles violently, thereby making it difficult to carry out the operation, while when said alkyl ether sulfate aqueous solution has a high concentration (Run No. 9) even the application of the present process can only concentrate the aqueous solution but can not deodorize it. In this connection, it is further noted that no deodorizing effects can be achieved in both cases wherein the heating temperature is low (Run No. 1) or is high (Run No. 3), even though the concentration of the alkyl ether sulfate aqueous solution falls within the range defined in accordance with the present invention.

We claim:

1. A process for deodorizing a polyoxyethylene alkyl ether sulfate aqueous concentrate, said aqueous concentrate containing from 60 to 80 wt.% of polyoxyethylene alkyl ether sulfate having the formula RO(CH$_2$CH$_2$O)$_n$-SO$_3$M, wherein R is alkyl having 8 to 18 carbon atoms, n is a number from 2 to 10 and M is a cation providing a water-soluble salt, the balance of said aqueous concentrate consisting essentially of water and the odorous components of unreacted alcohol and cyclic ether by-produced in the sulfation reaction for forming said polyoxyethylene alkyl ether sulfate, said process consisting essentially of the step of: subjecting said aqueous concentrate to a pressure in the range of from 50 to 400 mmHg, at a temperature of from 50° to 130° C., effective to evaporate said odorous components (and some of the water) from said aqueous concentrate, the treatment being carried out for a short period of time effective to prevent hydrolysis and coloration of said polyoxyethylene alkyl ether sulfate.

2. A process as claimed in claim 1 wherein said pressure is from 50 to 200 mmHg.

3. A process as claimed in claim 1 wherein said temperature is from 70° to 120° C.

4. A process as claimed in claim 1 wherein said composition is a reversed micelle where said polyoxyethylene alkyl ether sulfate forms a continuous phase and said water forms a dispersed phase.

5. A process as claimed in claim 1 wherein the concentration of said polyoxyethylene alkyl ether sulfate in said aqueous concentrate is increased by at least 5 wt.%.

6. A process as claimed in claim 1 wherein the concentration of said polyoxyethylene alkyl ether sulfate in said aqueous concentrate is increased to approximately 80 to 90 wt.%.

7. A process as claimed in claim 1 wherein M is selected from the group consisting of sodium, potassium, magnesium, monoethanolamine, diethanolamine and triethanolamine.

8. A process as claimed in claim 1 wherein said aqueous concentrate is flowed in the form of a thin film on a thin film evaporator while it is subjected to said temperature and said pressure.

* * * * *

UNITED STATES PATENT AND TRADEMARK OFFICE
CERTIFICATE OF CORRECTION

PATENT NO. : 4 411 815

DATED : October 25, 1983

INVENTOR(S) : Hideo ANDO et al

It is certified that error appears in the above-identified patent and that said Letters Patent is hereby corrected as shown below:

Column 6, line 4; before "and" delete "(".

line 5; after "water" delete ")".

Signed and Sealed this

Eighth Day of May 1984

[SEAL]

Attest:

GERALD J. MOSSINGHOFF

Attesting Officer

Commissioner of Patents and Trademarks